United States Patent [19]

Mertz et al.

[11] Patent Number: 4,689,429

[45] Date of Patent: Aug. 25, 1987

[54] LIQUID COPOLYESTER PLASTICIZERS DERIVED FROM 1,4-BUTANEDIOL AND A DICARBOXYLIC ACID MIXTURE

[75] Inventors: William J. Mertz; William L. O'Brien, both of Cincinnati, Ohio

[73] Assignee: National Distillers and Chemical Corporation, New York, N.Y.

[21] Appl. No.: 894,170

[22] Filed: Aug. 7, 1986

[51] Int. Cl.$^4$ ............................................. C07C 69/42
[52] U.S. Cl. .................... 560/199; 524/314; 560/204
[58] Field of Search ................. 560/199; 524/314

[56] References Cited

U.S. PATENT DOCUMENTS 3,907,863  9/1975  Voss ..................................... 560/199
4,122,057 10/1978  Lamont et al. ....................... 560/199
4,596,886  6/1986  Hasegawa et al. ................... 560/199

Primary Examiner—Werren B. Lone
Assistant Examiner—Vera C. Clarke
Attorney, Agent, or Firm—Kenneth D. Tremain; Gerald A. Baracka

[57] ABSTRACT

Liquid copolyesters useful as plasticizers for vinyl resins are provided. The copolyesters are obtained by the esterification of specific aliphatic dicarboxylic acid ester mixtures with 1,4-butanediol and an aliphatic saturated monofunctional alcohol. The copolyesters have acceptably low solidification points; they are resistant to hydrocarbon extraction; and they impart good low-temperature flexibility to PVC compositions plasticized therewith.

9 Claims, No Drawings

LIQUID COPOLYESTER PLASTICIZERS DERIVED FROM 1,4-BUTANEDIOL AND A DICARBOXYLIC ACID MIXTURE

BACKGROUND OF THE INVENTION

1. Field of the Invention

The present invention relates to liquid alcohol-terminated copolyesters obtained from 1,4-butanediol and mixed aliphatic dicarboxylic acids (or anhydride or ester thereof) and to their use as plasticizers for vinyl resins, particularly polyvinyl chloride (PVC).

2. Description of the Prior Art

Copolyester plasticizers for vinyl resins used in the manufacture of pressure sensitive electrical tapes must be resistant to hydrocarbon extraction, since adhesive backings are customarily applied with hydrocarbon diluents, and should impart good low temperature flexibility characteristics to the resin composition. Also, for ease of handling, the copolyesters are preferably liquids at room temperature and, more preferably, down to about 20° C. or below. This feature, while not necessarily related to the performance characteristics of the product, is an important consideration for commercial operations where the plasticizer is typically held in bulk storage tanks. In most instances, these tanks are not heated since this adds additional cost to the operation and can adversely affect the servicelife of the product.

Alcohol-terminated copolyesters derived from $C_{6-9}$ aliphatic dicarboxylic acids and mixtures of 1,4-butanediol and propylene glycol were developed to meet these requirements and have been extensively used throughout the industry. Both the $C_{6-9}$ dicarboxylic acid and the 1,4-butanediol/propylene glycol mixture were considered to be essential to obtain a copolyester having an acceptable balance of properties.

SUMMARY OF THE INVENTION

We have now quite unexpectedly discovered that alcohol-terminated copolyesters derived from 1,4-butanediol, as the sole diol, and aliphatic dicarboxylic acid mixtures containing a substantial amount of $C_5$ dicarboxylic acid (glutaric acid) are effective plasticizers for vinyl resins, particularly PVC, used in the manufacture of pressure sensitive electrical tape. The copolyesters have acceptably low solidification (freezing) points; they are resistant to hydrocarbon extraction; and they impart good low-temperature flexibility to PVC compositions plasticized therewith. This is unexpected since, other factors being equal, glutarate and adipate polyesters solidify at higher temperatures than azelate polyesters and vinyl resins plasticized therewith have poorer low temperature flexibility. It is even more surprising in view of the fact that in closely related copolyester compositions it has been shown that increasing the amount of 1,4-butanediol adversely affects the freezing point of the product.

The liquid copolyester plasticizers of the present invention are the reaction product of essentially stoichiometric amounts of an alcohol component consisting of 1,4-butanediol and an aliphatic saturated monofunctional alcohol having from 6 to 13 and, more preferably, 8 to 10 carbon atoms with an acid component which is a mixture of saturated aliphatic dicarboxylic acids, said mixture containing (a) from 40 to 60 weight percent $C_5$ dicarboxylic acid or methyl ester thereof;

(b) from 40 to 60 percent by weight $C_6$ and $C_{9-11}$ dicarboxylic acids or methyl esters thereof present in a ratio from 1:1 to 1:4; and (c) 10 percent or less other dicarboxylic acids in the range $C_{4-15}$ or methyl esters thereof.

The copolyesters typically have solidification points less than 20° C., acid values less than 3, hydroxyl values less than 25 and are advantageously utilized for the plasticization of PVC at levels from about 40 to 70 phr.

DETAILED DESCRIPTION OF THE INVENTION

The improved liquid copolyester plasticizers of the present invention are the reaction product of essentially stoichiometric amounts of an alcohol (hydroxylic) component and an acid (carboxylic) component. The alcohol component is a mixture of 1,4-butanediol and a monofunctional alcohol chain terminator. The acid component is a mixture of aliphatic saturated dicarboxylic acids wherein $C_5$, $C_6$, and $C_{9-11}$ dicarboxylic acids are the predominant acids and are present in specified ratios.

1,4-Butanediol is employed to obtain the copolyester plasticizers of the invention. No other diols are utilized with the 1,4-butanediol. The fact that copolyesters having acceptable low temperature properties are obtained in the absence of a second diol component is unexpected in view of the heretofore observed results obtained with closely related copolyester products.

An aliphatic monofunctional alcohol is employed with the 1,4-butanediol as a chain stopper, i.e., terminator. Branched or linear aliphatic saturated monofunctional alcohols having from 6 to 13 carbon atoms and, more preferably, from 8 to 10 carbon atoms are generally utilized for this purpose. Representative monofunctional alcohols which can be used with the 1,4-butanediol include 2-ethylhexanol, isooctyl alcohol, isodecyl alcohol, tridecyl alcohol, n-hexanol, n-decanol, n-octanol, and the like. Particularly useful plasticizer compositions are obtained using mixtures of 1,4-butanediol and 2-ethylhexanol.

The acid component reacted with the 1,4-butanediol and monofunctional alcohol to obtain the improved liquid copolyester plasticizers is a mixture of $C_{4-15}$ saturated aliphatic dicarboxylic acids. The dicarboxylic acid mixture necessarily contains a substantial amount of glutaric ($C_5$) acid, adipic ($C_6$) acid, and $C_{9-11}$ saturated aliphatic dicarboxylic acid(s). As employed herein, the term $C_{9-11}$ dicarboxylic acid is intended to encompass situations where either azelaic acid, sebacic acid or undecanedioc acid is present individually or, as is more generally the case, situations where two or more of these acids are present in the dicarboxylic acid mixture. The $C_5$, $C_6$, and $C_{9-11}$ acids constitute the bulk of the dicarboxylic acids present in the mixture and are present in specified amounts.

More specifically, the dicarboxylic acid mixture will contain (a) from 40 to 60 percent by weight $C_5$ acid, (b) from 40 to 60 percent by weight $C_6$ and $C_{9-11}$ acids present in a ratio from 1:1 to 1:4, and (c) 10 percent or less other dibasic acids in the range $C_{4-15}$ (exclusive of the $C_5$, $C_6$, and $C_{9-11}$ dicarboxylic acids). In view of the substantial quantity of glutaric and adipic acids present in the mixture and the adverse effect on the solidification point and low temperature flexibility of PVC compositions formulated therewith which is observed with these acids in similar compositions, the results obtained with the present invention are truly surprising. In a particularly useful embodiment of the invention, (a) constitutes 45 to 55 percent by weight of the mixture, (b) constitutes from 45 to 55 percent by weight of the mixture, and the ratio of $C_6$ to $C_{9-11}$ dicarboxylic acids range from 1:1 to 1:3, and the remaining dicarboxylic acids (c) in the range $C_{4-15}$ are present in an amount less than about 6 percent by weight. Most generally, dicarboxylic acids of $C_{12}$ or above constitute 1 percent or less of the mixture.

It will be obvious to those skilled in the art that the various art-recognized equivalents of the aforementioned dicarboxylic acids, i.e., anhydrides and lower alkyl esters thereof, can also be employed for the preparation of the present copolyester products. Therefore, as used herein the term acid is intended to encompass these acid derivatives. Methyl esters are particularly advantageous for the preparation of the copolyesters. Mixtures of acids, anhydrides, and esters can also be reacted to obtain useful plasticizer products.

The dicarboxylic acid mixtures can be obtained by blending the individual acid components or mixtures of said acids. The source of the acids or acid derivatives and the manner by which the dicarboxylic acid mixture is produced is of no consequence so long as the resulting mixture contains the specified acids or acid derivatives in the prescribed ratios. Mixtures of acids obtained as by-products from various manufacturing operations and which contain one or more of the necessary acid components may be advantageously utilized. For example, mixed dimethyl esters of adipic and glutaric acids obtained as a co-product from the manufacture of adipic acid can be conveniently blended with azelaic acid, sebacic acid or undecanedioic acid or by-product streams containing $C_9$, $C_{10}$, and/or $C_{11}$ dicarboxylic acids as the major constituent to obtain the final dicarboxylic acid (ester) mixture.

Although the individual reactants employed to obtain the plasticizers of this invention are known for the preparation of polyesters, the present copolyester compositions are novel as a result of the particular combination of reactants necessary and the unique and unexpected properties obtained. Whereas the skilled artisan would expect the introduction of substantial quantities of $C_5$ and $C_6$ dicarboxylic acids to have a detrimental effect on the solidification point of the copolyester and the low temperature flexibility of vinyl compositions plasticized therewith, Applicants have quite unexpectedly found that this is not the case when their specific dicarboxylic acid mixtures are employed with 1,4-butanediol as the sole diol component. Furthermore, the results are even more unexpected in view of the fact that it has generally been recognized in the art that a second diol must be used with 1,4-butanediol to obtain copolyesters having acceptable solidification points and that as the amount of 1,4-butanediol is increased the solidification (freezing) point is raised. Quite unexpectedly, however, Applicants have discovered that the instant copolyesters have acceptably low freezing points; they are resistant to hydrocarbon extraction; and they impart good low temperature flexibility to PVC compositions plasticized therewith.

The copolyester plasticizers of the invention are prepared using conventional reaction techniques. Reaction of the acid and alcohol components to obtain the desired copolyesters is carried out in standard esterification equipment following established esterification procedures. Typically, all of the reactants are charged to a suitable esterification kettle and heated at atmospheric pressure at temperatures on the order of about 150°–250° C. for a period of time sufficient to substantially complete the esterification. The reaction may be driven to completion by distillation in vacuum (typically 2–50 mm Hg absolute at 200°–250° C.) until the desired acid value is obtained. The vacuum distillation removes the final traces of water, any excess 1,4-butanediol or monofunctional alcohol and small amounts of other volatile materials. The plasticizer is then cooled and is normally ready for use.

If an improvement in color is desired, the copolyester may be bleached by any of the well known and accepted bleaching methods, e.g., using hydrogen peroxide or hypochlorite. Alternatively, the copolyester can be decolorized by filtering through a filter aid, charcoal or bleaching clay.

Whereas the esterification reaction is generally carried out without use of a catalyst, where shorter reaction times are desired, a catalyst may be advantageous. Known esterification catalysts, such as phosphoric acid, p-toluenesulfonic acid, stannous oxalate, alkyltin oxides, or the like can be utilized in small amounts and facilitate the reaction. When esterification is complete, the catalyst may be deactivated or removed by filtering or other conventional means.

Inert diluents such as benzene, toluene, xylene, and the like can be employed for the reaction, however, they are not necessary. In fact, it is generally considered to be desirable to conduct the reaction without diluents since the copolyester can be directly used as it is obtained from the reactor.

The 1,4-butanediol typically comprises from about 70 to about 90 equivalent percent of the total alcohol equivalents. The aliphatic saturated monofunctional alcohol is employed in an amount from about 10 to about 30 equivalent percent, based on the total equivalents of alcohol. In accordance with the standard practice in reactions of this type, a slight excess of 1,4-butanediol and/or monofunctional alcohol is generally charged to aid in driving the esterification to completion. However, essentially stoichiometric amounts of the acid component and the alcohol component are reacted as evidenced by the acid value and hydroxyl value of the resulting product. Acid values of the copolyesters are generally less than 3 and hydroxyl values are typically less than 25. The resulting liquid copolyesters have number average molecular weights in the range 700 to about 1800 and 100° F. kinematic viscosities in the range 350 to about 1250 centistokes. Solidification points of the copolyesters are generally 20° C. or below, and more preferably, 15° C. or below.

The copolyester plasticizer compositions of the present invention are useful for a wide variety of vinyl resins including PVC homopolymers and PVC copolymers wherein one or more other ethylenically unsaturated comonomers is copolymerized with vinyl chloride. Such comonomers can include: vinyl bromide; vinyl acetate; vinylidene chloride; lower allyl esters; vinyl alkyl ethers; acrylonitrile and methacrylonitrile; acrylic acid and methacrylic acid; acrylic and methacrylic esters such as methyl acrylate, ethyl acrylate and methyl methacrylate; styrene; and the like. The copolyesters are particularly useful for the plasticization of PVC homopolymers and copolymers of vinyl chloride with vinyl acetate, vinyl chloride with vinyl butyrate, vinyl chloride with vinyl propionate, vinyl chloride with methyl methacrylate, vinyl chloride with vinylidene chloride and vinyl chloride with two or more comonomers, such as mixtures of vinylidene chloride and 2-ethylhexylacrylate, particularly when the copolymers contain 75 percent by weight or more bound vinyl chloride.

The amount of copolyester used can be widely varied and will range from about 40 up to about 70 parts by weight per 100 parts by weight of the vinyl chloride homopolymer or copolymer. The copolyesters are particularly useful for the plasticization of PVC pressure sensitive electrical tape. The copolyesters can be utilized in combination with other plasticizers. When combined with other plasticizers, the total amount of plasticizer will generally fall within the above-prescribed ranges.

The copolyesters of this invention are also compatible with other known compounding ingredients commonly employed in the formulation of PVC. Such ingredients include stabilizers to protect the resin from the deleterious effects of oxidative, thermal and photochemical degradation, fillers, pigments, dyes, lubricants, and other processing aids. As is evident to those skilled in the art of compounding and formulating PVC, the type and amount of compounding ingredients used will be determined by the physical properties desired.

The following examples illustrate the invention more fully. They are not, however, intended as a limitation on the scope thereof. In the examples, all weights and percentages are on a weight basis unless otherwise indicated.

EXAMPLE 1

A typical copolyester plasticizer of the invention was prepared by charging the following:

| Reactant | Equivalent Percent |
| --- | --- |
| Methyl Esters of Mixed Dicarboxylic Acids* | 100 |
| 1,4-Butanediol | 96** |
| 2-Ethylhexanol | 24** |

*The dicarboxylic acid mixture was comprised as follows: 49.1 wt. % $C_5$; 14.9 wt. % $C_6$; 0.5 wt. % $C_7$; 1.2 wt. % $C_8$; 30.3 wt. % $C_9$; 1.0 wt. % $C_{10}$; 2.4 wt. % $C_{11}$; 0.3 wt. % $C_{12}$; 0.2 wt. % $C_{13}$; 0.1 wt. % $C_{14}$; and 0.1 wt. % $C_{15}$.
**The charge included 20% equivalent excess 1,4-butanediol and 20% equivalent excess 2-ethylhexanol to aid in driving the reaction to completion.

The above reactants were charged to a three-necked, round bottom flask equipped with a suitable agitator, a thermometer, and a medium length Vigreaux distillation column and condenser. The condenser was arranged so that material could be distilled from the reaction at either atmospheric or reduced pressure. A small amount $H_3PO_2$ (0.01 weight percent) and dibutyltin diacetate (0.03 weight percent) were added to the reactor and the mixture slowly heated to about 220° C. while removing methanol. The pressure was then gradually reduced to about 5 Torr and the temperature maintained at 220°–223° C. so that controlled distillation was achieved. The reaction was followed by measuring the acid value (AV) of the reaction mixture and terminated when the AV was less than 0.2. The reaction mixture was then cooled to room temperature and filtered using a diatomaceous earth filter aid to remove catalyst and other impurities. The final copolyester product had an average molecular weight of about 1000, AV of 0.2, hydroxyl value (OHV) of 19.6 and kinematic viscosity at 100° F. of 612 cSt. The copolyester had a solidification point of −4° C. as determined in accordance with ASTM Test Method D97-57. The clear, essentially colorless liquid was useful as a plasticizer without further modification or processing and was readily incorporated into PVC resin homopolymers and copolymers using conventional processing equipment to produce clear pliable sheets.

A standard PVC resin formulation was prepared in accordance with the following recipe:

|  | PHR |
| --- | --- |
| PVC resin (GEON 102 F5) | 100 |
| Barium-Cadmium Stabilizer (FERRO 1820) | 2 |
| Phosphite Stabilizer (FERRO 904) | 1 |
| Copolyester Plasticizer | 56 |

The ingredients were milled for about 10 minutes on a standard two-roll rubber mill (6×12 inch rolls heated to about 170° C. and set for a sheet thickness of about 0.25 inch). Sheets of uniform 20 mil thickness were then prepared by pressing using a chrome-plated ASTM D-412 mold at about 177° C. for 6 minutes at 1500 psi. Test specimens were cut from the pressed sheet and physical properties determined using conventional test methods. Properties of the plasticized resin were as follows:

| Elongation (%) | 362 |
| --- | --- |
| 100% Modulus (psi) | 1200 |
| Tensile Strength (psi) | 3137 |
| Roll Spew (5 hours at RT) | None |
| Brittle Point (°C.) (ASTM D-746-57T) | −33 |

The plasticized PVC resin was also evaluated to determine resistance to hydrocarbon extraction. For this test, duplicate 2½ inch diameter samples were die cut from the 20 mil pressed sheet and the initial weight determined for each. The samples were then immersed on racks in 450 mls hexane (Skellysolve "B") and extracted for 24 hours at 25° C. The samples were then removed and dried in a circulating air oven at 90° C. for 2 hours. They were then conditioned at 72° F. for 0.5 hour and reweighed. Weight loss was calculated as follows:

$$\text{Percent weight loss} = \frac{W_1 - W_2}{W_1} \times 100$$

where:
$W_1$ initial weight
$W_2$ weight after extraction
Under the conditions of this test, a weight percent loss of 3 percent or less is considered to be acceptable. The PVC polymer plasticized with the copolyester of this invention gave a weight loss of 2.69 percent.

EXAMPLE II

To demonstrate the versatility of the invention and the ability to vary the acid component within the prescribed range, Example I was repeated using a mixture of dicarboxylic acids and methyl esters of dicarboxylic acids. The acid component was obtained by blending a commercially available co-product obtained from the manufacture of adipic acid (DBE-2 manufactured by E. I. du Pont de Nemours & Co.) and a commercially available azelaic acid. The composition of the dicarboxylic acid/ester blend was as follows: 48.7 wt. % $C_5$, 15.2 wt. % $C_6$, 0.9 wt. % $C_7$, 1.3 wt. % $C_8$, 30.7 wt. % $C_9$, 0.9 wt. % $C_{10}$, 2.2 wt. % $C_{11}$. The equivalent percent of the reactants used and the reaction procedure was the same as described in Example I. The resulting copolyester had an acid value of 0.7, hydroxyl value of 12.2, 100° F. kinematic viscosity of 530 centistokes, and solidification point of −1° C.

When formulated with PVC in accordance with the recipe and procedure set forth in Example I, the resulting plasticized PVC composition had the following properties:

| | |
|---|---|
| Elongation (%) | 310 |
| 100% Modulus (psi) | 1400 |
| Tensile Strength (psi) | 3150 |
| Roll Spew (5 hours at RT) | None |
| Brittle Point (°C.) (ASTM D-746-57T) | −27 |
| Percent Weight Loss Upon Hexane Extraction | 2.44 |

EXAMPLE III

For comparison purposes and to demonstrate the need to employ a mixture of dicarboxylic acids when 1,4-butanediol is the sole diol employed, a copolyester was prepared following the procedure of Example I using the following reactant charge:

| Reactants | Equivalent Percent |
|---|---|
| Adipic Acid (99.9%) | 100 |
| 1,4-Butanediol | 96 |
| 2-Ethylhexanol | 24 |

The resulting copolyester (AV=1.0; OHV=10.2) was a solid at room temperature (approx. 25° C. and was therefore unacceptable for use. Copolyester products which were solid at room temperature were also obtained by substituting essentially pure azelaic acid or essentially pure glutaric acid for the adipic acid.

EXAMPLE IV

To demonstrate the criticality of the prescribed dicarboxylic acid mixtures and, more specifically, mixtures containing a substantial amount of glutaric acid the following comparative example was carried out. For this example, a copolyester was prepared in accordance with the procedure of Example I using 1,4-butanediol as the sole diol and 2-ethylhexanol as the terminator. The dicarboxylic acid mixture used had the following analysis: 0.6 wt. % $C_5$, 63.5 wt. % $C_6$, 1.0 wt. % $C_7$, 1.3 wt. % $C_8$, 30.6 wt. % $C_9$, 0.9 wt. % $C_{10}$, and 2.2 wt. % $C_{11}$. Equivalent percents of reactants were the same as employed in the previous examples. The resulting copolyester (AV=1.0; OHV=12.5) was a solid at room temperature and was therefore unacceptable. It is apparent from the foregoing that a mixture of adipic acid and glutaric acid is necessary if liquid polyesters are to be obtained using 1,4-butanediol as the sole diol component.

EXAMPLE V

A copolyester plasticizer was prepared in accordance with the standard procedure using a mixed dicarboxylic acid containing 52.1 weight percent glutaric acid, 15.6 weight percent adipic acid, and 32.3 weight percent sebacic acid. The reactant charge and conditions were the same as described in Example I. The resulting liquid copolyester product had an acid value of 0.25, hydroxyl value of 11.4, 100° F. viscosity of 899 centistokes, and solidification point of 4° C. PVC compositions were prepared using the copolyester product in accordance with the recipe and procedure set forth in Example I and had the following properties:

| | |
|---|---|
| Elongation (%) | 338 |
| 100% Modulus (psi) | 1255 |
| Tensile Strength (psi) | 3082 |
| Brittle Point (°C.) (ASTM D-746-57T) | −30 |
| Percent Weight Loss Upon Hexane Extraction | 2.77 |

We claim:

1. A liquid copolyester plasticizer having a solidification point of 20° C. or below obtained by the esterification of an alcohol component consisting of 1,4-butanediol and an aliphatic saturated monofunctional alcohol having from 6 to 13 carbon atoms with an acid component which is a mixture of saturated aliphatic dicarboxylic acids, said mixture containing
   (a) from 40 to 60 weight percent $C_5$ dicarboxylic acid or methyl ester thereof;
   (b) from 40 to 60 percent by weight $C_6$ and $C_{9-11}$ dicarboxylic acids or methyl esters thereof present in a ratio from 1:1 to 1:4; and
   (c) 10 percent or less other dicarboxylic acids in the range $C_{4-15}$ or methyl esters thereof, exclusive of the $C_5$, $C_6$, and $C_{9-11}$ dicarboxylic acids.

2. The liquid copolyester plasticizer of claim 1 which has a 100° F. kinematic viscosity in the range 350 to 1250 centistokes and number average molecular weight in the range 700 to 1800.

3. The liquid copolyester plasticizer of claim 1 wherein essentially stoichiometric amounts of the acid component and alcohol component are reacted to an acid value less than 3 and hydroxyl value less than 25.

4. The liquid copolyester plasticizer of claim 3 wherein the 1,4-butanediol comprises form 70 to 90 equivalent percent of the total alcohol equivalents and the aliphatic saturated monofunctional alcohol comprises from about 10 to 30 equivalent percent of the total alcohol equivalents.

5. The liquid copolyester plasticizer of claim 4 wherein the aliphatic unsaturated monofunctional alcohol contains from 8 to 10 carbon atoms.

6. The liquid copolyester plasticizer of claim 5 wherein the aliphatic saturated monofunctional alcohol is 2-ethylhexanol.

7. The liquid copolyester plasticizer of claim 4 wherein the acid component contains (a) 45 to 55 percent by weight $C_5$ dicarboxyic acid or methyl ester thereof, (b) 45 to 55 percent by weight $C_6$ and $_{9-11}$ dicarboxylic acids or methyl esters thereof peresent in a ratio of 1:1 to 1:3, and (c) less than about 6 percent by weight $C_{4-15}$ dicarboxylic acids or methyl esters thereof, exclusive of the $C_5$, $C_6$, and $C_{9-11}$ dicarboxylic acids.

8. The liquid copolyester plasticizer of claim 7 wherein the acid component contains 1 percent or less dicarboxylic acids having 12 or more carbon atoms or methyl esters thereof.

9. A liquid copolyester plasticizer having a solidification point of 20° C. or below, acid value less than 3, and hydroxyl value less than 25 which is the reaction product of essentially stoichiometric amounts of a mixture of 1,4-butanediol and 2-ethylhexanol, said 1,4-butanediol comprising 70 to 90 equivalent percent of total alcohol equivalent and said 2-ethylhexanol comprising 10 to 30 equivalent percent of the total alcohol equivalents, and a mixture of saturated aliphatic dicarboxylic acids, said dicarboxylic acid mixture containing (a) 45 to 55 percent by weight $C_5$ dicarboxylic acid or methyl ester thereof, (b) 45 to 55 percent by weight $C_6$ and $C_{9-11}$ dicarboxylic acids or methyl esters thereof, the weight ratio of said $C_6$ to said $C_{9-11}$ dicarboxylic acids ranging from 1:1 to 1:3, and (c) less than 6 percent by weight $C_{4-15}$ dicarboxylic acids or methyl esters thereof, exclusive of the $C_5$, $C_6$, and $C_{9-11}$ dicarboxylic acids.

* * * * *